United States Patent [19]

Thomas et al.

[11] Patent Number: 5,380,449
[45] Date of Patent: Jan. 10, 1995

[54] STABILIZED DICHLOROTRIFLUOROETHANE REFRIGERATION COMPOSITIONS

[75] Inventors: Raymond H. P. Thomas; Ruth H. H. Chen, both of Amherst; Kenneth Harris, Buffalo, all of N.Y.

[73] Assignee: AlliedSignal Inc., Morristownship, Morris County, N.J.

[21] Appl. No.: 883,058

[22] Filed: May 8, 1992

Related U.S. Application Data

[62] Division of Ser. No. 682,156, Apr. 5, 1991, abandoned.

[51] Int. Cl.$^6$ ................................................. C09K 5/00
[52] U.S. Cl. .................................. 252/68; 252/52 R; 252/52 A; 570/116
[58] Field of Search ............... 570/116; 252/68, 52 A, 252/52 R

[56] References Cited

U.S. PATENT DOCUMENTS

| | | | |
|---|---|---|---|
| 3,025,331 | 3/1962 | Dial | 570/116 |
| 4,248,726 | 2/1981 | Uchimuma et al. | 252/52 |
| 4,267,064 | 5/1981 | Sasaki et al. | 252/52 |
| 4,431,557 | 2/1984 | Shimizu et al. | 252/52 |
| 4,443,349 | 4/1984 | Snyder et al. | 252/49.9 |
| 4,755,316 | 7/1988 | Magid et al. | 252/68 |
| 4,812,246 | 3/1989 | Yabe | 252/327 |
| 4,851,144 | 7/1989 | McGraw et al. | 252/52 |
| 4,900,463 | 2/1990 | Thomas et al. | 252/54 |
| 4,948,525 | 8/1990 | Sasaki et al. | 252/54 |
| 4,959,169 | 9/1990 | McGraw et al. | 252/68 |
| 4,971,712 | 11/1990 | Gorski et al. | 252/52 |
| 4,975,212 | 12/1990 | Thomas et al. | 252/54 |
| 5,084,196 | 1/1992 | Seiki | 252/68 |
| 5,108,632 | 4/1992 | Thomas et al. | 252/52 A |
| 5,120,459 | 6/1992 | Kalota et al. | 252/54 |
| 5,156,768 | 10/1992 | Thomas et al. | 252/52 A |

FOREIGN PATENT DOCUMENTS

| | | |
|---|---|---|
| 2943446A1 | 5/1980 | Germany . |
| 51795 | 3/1982 | Japan . |
| 85324 | 5/1982 | Japan ................................. 570/116 |
| 83-21170K | 1/1983 | Japan . |
| 84-008052 | 11/1983 | Japan . |
| 96684 | 5/1985 | Japan . |
| 60-130696 | 7/1985 | Japan . |
| 179699 | 10/1985 | Japan . |
| 281199 | 12/1988 | Japan . |
| 56630 | 3/1989 | Japan . |
| 56631 | 3/1989 | Japan . |
| 56632 | 3/1989 | Japan . |
| 89-110611 | 3/1989 | Japan . |
| 118598 | 5/1989 | Japan . |
| 128943 | 5/1989 | Japan . |
| 128944 | 5/1989 | Japan . |
| 128945 | 5/1989 | Japan . |
| 89-189490 | 5/1989 | Japan . |
| 139539 | 6/1989 | Japan . |
| 1193394 | 8/1989 | Japan . |
| 265042 | 10/1989 | Japan . |
| 102296 | 4/1990 | Japan . |
| 91-159429 | 4/1991 | Japan . |
| WO89/07129 | 8/1989 | WIPO . |

*Primary Examiner*—Prince Willis, Jr.
*Assistant Examiner*—James M. Silberman
*Attorney, Agent, or Firm*—Karen A. Harding; Jay P. Friedenson; Melanie L. Brown

[57] ABSTRACT

Trichlorofluoromethane refrigeration systems use mineral oil to lubricate the compressor. We have found that the use of 1,1-dichloro-2,2,2-trifluoroethane and mineral oil results in the formation of 1-chloro-2,2,2-trifluoroethane; in the absence of mineral oil, the use of 1,1-dichloro-2,2,2-trifluoroethane does not result in the formation of 1-chloro-2,2,2-trifluoroethane. We have found an additive which substantially reduces the formation of 1-chloro-2,2,2-trifluoroethane. Thus, the present invention provides a composition comprising: (a) 1,1-dichloro-2,2,2-trifluoroethane, (b) hydrogen-contributing lubricant: and (c) a composition comprising: (i) at least one phenol and (ii) at least one aromatic or fluorinated alkyl epoxide wherein the composition (c) substantially reduces the decomposition of 1,1-dichloro-2,2,2-trifluoroethane.

8 Claims, No Drawings

STABILIZED DICHLOROTRIFLUOROETHANE REFRIGERATION COMPOSITIONS

This application is a divisional of application Ser. No. 682,156 filed Apr. 5, 1991 now abandoned.

FIELD OF THE INVENTION

The present invention relates to stabilized compositions. More particularly, the present invention relates to stabilized dichlorotrifluoroethane. More particularly, the present invention relates to stabilized refrigeration compositions of 1,1-dichloro-2,2,2-trifluoroethane (known in the art as HCFC-123) and hydrogen-contributing lubricant.

BACKGROUND OF THE INVENTION

The art is continually seeking new hydrochlorofluorocarbons to be used in many applications. Hydrochlorofluorocarbons are considered to be stratospherically safe substitutes for presently used fully halogenated chlorofluorocarbons. The latter are suspected of causing environmental problems in connection with the earth's protective ozone layer. Mathematical models have substantiated that hydrochlorofluorocarbons, such as dichlorotrifluoroethane, will not adversely affect atmospheric chemistry, being negligible contributors to ozone depletion and to green-house global warming in comparison to the fully halogenated species.

Dichlorotrifluoroethane is being considered for use in many applications including as a solvent and a refrigerant. Dichlorotrifluoroethane hydrolyzes to form hydrogen chloride. While dichlorotrifluoroethane is useful in many applications, dichlorotrifluoroethane should be stabilized against possible changes during storage and use. When metallic materials are present, the problem is worsened because the metal acts as a catalyst and causes the hydrolysis of dichlorotrifluoroethane to increase exponentially. Also, ultraviolet light decomposes dichlorotrifluoroethane.

In addition to dichlorotrifluoroethane reacting with water to form acids such as hydrogen chloride and hydrogen fluoride, dichlorotrifluoroethane also reacts with alcoholic hydroxyl groups to form aldehydes and ketones. Known stabilizers for compositions of 1,1-dichloro-2,2,2-trifluoroethane and alcohol include: epoxy compounds as taught by Kokai Patent Publication 56,630 published Mar. 3, 1989; combinations of styrene and epoxy compounds as taught by Kokai Patent Publication 56,631 published Mar. 3, 1989; combinations of styrene compounds and phenols as taught by Kokai Patent Publication 56,632 published Mar. 3, 1989; combinations of epoxy and styrene compounds and phenols as taught by Kokai Patent Publication 128,944 published May 22, 1989; hydrocarbons containing nitro groups as taught by Kokai Patent Publication 128,944 published May 22, 1989; combinations of hydrocarbons containing nitro groups and epoxy compounds as taught by Kokai Patent Publication 128,945 published May 22, 1989; and phenols as taught by Kokai Patent Publication 265,042 published Oct. 23, 1989. Kokai Patent Publication 139,539 teaches 1,2-dichloro-1,1,2-trifluoroethane based azeotropic compositions which are stabilized with at least one of nitro compounds, phenols, amines, ethers, amylenes, esters, organic phosphites, epoxides, furans, alcohols, ketones, and triazoles.

Because dichlorotrifluoroethane may be used alone in many applications, it would be advantageous to have a stabilized dichlorotrifluoroethane. This ideally stabilized dichlorotrifluoroethane could then be used in many applications wherein dichlorotrifluoroethane is typically exposed to water, metallic materials, and ultraviolet light.

Dichlorotrifluoroethane has three isomers including 1,1-dichloro-2,2,2-trifluoroethane (known in the art as HCFC-123) and 1,2-dichloro-1,1,2-trifluoroethane (known in the art as HCFC-123a). R123 may replace trichlorofluoromethane (known in the art as R11) in many applications because environmental concerns over the use of R11 exist. R11 is currently used as a refrigerant in closed loop refrigeration systems; many of these systems are air-conditioning systems. R123 has properties similar to those of R11 so that it is possible to substitute R123 for R11 in refrigeration applications with minimal changes in equipment being required.

A problem arises in such a substitution. Refrigeration systems which use R11 generally use mineral oils to lubricate the compressor. We have found that the use of R123 and mineral oil results in the formation of 1-chloro-2,2,2-trifluoroethane (known in the art as HCFC-133a); in the absence of mineral oil, the use of R123 does not result in the formation of HCFC-133a. E. Long et al., *Toxicol. Appl. Pharmacl.* 72, 15 (1984) report that HCFC-133a is an animal carcinogen. Understandably, the potential presence of a known animal carcinogen is unacceptable in any commercial system.

As such, the need exists in the art for an additive which substantially minimizes the reaction of R123 with mineral oil.

Kokai Patent Publication 128,943 published May 22, 1989 teaches a method for stabilizing a hydrogen-containing furon such as R123 against alcoholic hydroxyl groups. The reference teaches that a three-component stabilizer system of a styrenic compound, a phenol, and an epoxy can be used for the storage stability of polyol which contains the hydrogen-containing furon as the foaming agent. The reference lists chlorotrifluoroethane as a useful hydrogen-containing furon.

Kokai Patent Publication 128,944 published May 22, 1989 teaches a method for stabilizing a hydrogen-containing furon such as R123 against alcoholic hydroxyl groups. The reference teaches that a stabilizer of a nitro-containing hydrocarbon such as nitromethane, 1-nitropropane, 2-nitropropane, or nitrobenzene can be used for the storage stability of polyol which contains the hydrogen-containing furon as the foaming agent. The reference lists chlorotrifluoroethane as a useful hydrogen-containing furon.

Kokai Patent Publication 128,945 published May 22, 1989 teaches a method for stabilizing a hydrogen-containing furon such as 1,1-dichloro-2,2,2-trifluoroethane against alcoholic hydroxyl groups. The reference teaches that a two-component stabilizer system of a nitro-containing hydrocarbon and an epoxy compound can be used for the storage stability of polyol which contains the hydrogen-containing furon as the foaming agent. The reference lists chlorotrifluoroethane as a useful hydrogen-containing furon.

In an attempt to solve this problem, we considered epoxides as taught by Kokai Patent Publication 179,699 published Oct. 12, 1984; and Kokai Patent Publication 281,199 published Dec. 11, 1988. As shown in Comparatives D through F below, we added epoxides to compositions of R123 and mineral oil and found that epoxides alone were ineffective in substantially reducing the reaction of R123 with mineral oil.

Also in an attempt to solve this problem, we considered phenols as listed in commonly assigned U.S. Pat. No. 4,755,316; Kokai Patent Publication 281,199 published Dec. 11, 1988; U.S. Pat. Nos. 4,812,246 and 4,851,144; commonly assigned U.S. Pat. No. 4,900,463; Kokai Patent Publication 102,296 published Apr. 13, 1990; U.S. Pat. No. 4,959,169; and commonly assigned U.S. Pat. No. 4,975,212. As shown in Comparatives B and C below, we added phenols to compositions of R123 and mineral oil and found that the phenols alone were ineffective in substantially reducing the reaction R123 with mineral oil.

We were then surprised to find that the combination of aromatic epoxide and phenol is effective in substantially reducing the reaction of R123 with mineral oil.

U.S. Pat. Nos. 4,248,726; 4,267,064; and 4,431,557 teach the addition of epoxides to compositions of refrigerants and lubricants. The references also teach that known additives such as phenol or amine type antioxidants; sulphur or phosphorus type oiliness improvers; silicone type antifoam agents; metal deactivators such as benzotriazole, amines, and acid esters; and load carrying additives such as phosphoric acid esters, phosphorous acid esters, thiophosphoric acid esters, organic sulfur compounds, and organic halogen compounds can be used. These references do not teach or suggest the present invention.

U.S. Pat. No. 4,948,525 teaches that known refrigerator oil additives such as phenol-type antioxidants such as di-tert-butyl-p-cresol; amine-type antioxidants such as phenyl-α-naphthylamine and N,N'-di(2-naphthyl)-p-phenylenediamine; load resistant additives such as zinc dithiophosphate, chlorinated paraffin, fatty acids, and sulfur type load resistant compounds; silicone-type antifoaming agents; metal inactivators such as benzotriazole; and hydrogen chloride captors such as glycidyl methacrylate and phosphite esters may be used in refrigeration compositions. The reference states that these additives may be used singly or jointly but does not teach or suggest the present invention.

SUMMARY OF THE INVENTION

The present invention provides a composition comprising: (a) dichlorotrifluoroethane and (b) a composition comprising stabilizing amounts of (i) at least one phenol and (ii) at least one aromatic or fluorinated alkyl epoxide. The stabilized dichlorotrifluoroethane can be used in any application wherein dichlorotrifluoroethane is typically exposed to water, metallic materials, or ultraviolet light.

The present invention also provides a composition comprising: (a) 1,1-dichloro-2,2,2-trifluoroethane; (b) hydrogen-contributing lubricant; and (c) a composition comprising: (i) at least one phenol and (ii) at least one aromatic or fluorinated alkyl epoxide wherein the composition (c) substantially reduces the decomposition of 1,1-dichloro-2,2,2-trifluoroethane. As those skilled in the art know, 1-chloro-2,2,2-trifluoroethane has one less chlorine atom and one more hydrogen atom than 1,1-dichloro-2,2,2-trifluoroethane. Although we do not fully understand the mechanism as to the formation of 1-chloro-2,2,2-trifluoroethane from a combination of 1,1-dichloro-2,2,2-trifluoroethane and a lubricant such as mineral oil, we believe that the mineral oil must be contributing a hydrogen. As such, the phrase "hydrogen-contributing lubricant" as used herein means any lubricant which contributes a hydrogen. Examples of preferred hydrogen-contributing lubricants which are useful in the present invention include mineral oil, alkyl benzenes, and esters.

Because the stabilizer system of the present invention can be added to the dichlorotrifluoroethane alone, to the dichlorotrifluoroethane and hydrogen-contributing lubricant together, or to the hydrogen-contributing lubricant alone, the present invention also provides a composition comprising: (a) hydrogen-contributing lubricant and (b) a composition comprising stabilizing amounts of (i) at least one phenol and (ii) at least one aromatic or fluorinated alkyl epoxide.

Other advantages of the present invention will become apparent from the following description and the appended claims.

DESCRIPTION OF THE PREFERRED EMBODIMENTS.

Although any isomer of dichlorotrifluoroethane can be use in the present invention, preferably, 1,1-dichloro-2,2,2-trifluoroethane is used. Commercially available 1,1-dichloro-2,2,2-trifluoroethane can be used or 1,1-dichloro-2,2,2-trifluoroethane may be prepared by any known method including that taught by commonly assigned U.S. Pat. No. 4,145,368 which is incorporated herein by reference.

For the stabilized dichlorotrifluoroethane, any phenol can be used. Preferred phenols include:
4,4'-methylenebis(2,6-di-tert-butylphenol);
4,4'-bis(2,6-di-tert-butylphenol);
2,2- or 4,4-biphenyldiols including 4,4'-bis(2-methyl-6-tert-butylphenol); derivatives of 2,2- or 4,4-biphenyldiols; 2,2'-methylenebis(4-ethyl-6-tertbutylpheol);
2,2'-methylenebis(4-methyl-6-tert-butylphenol);
4,4,-butylidenebis(3-methyl-6-tert-butylphenol);
4,4,-isopropylidenebis(2,6-di-tert-butylphenol);
2,2'-methylenebis(4-methyl-6-nonylphenol);
2,2'-isobutylidenebis(4,6-dimethylphenol);
2,2'-methylenebis(4-methyl-6-cyclohexylphenol);
2,6-di-tert-butyl-4-methylphenol;
2,6-di-tert-butyl-4-ethylphenol;
2,4-dimethyl-6-tert-butylphenol;
2,6-di-tert-α-dimethylamino-p-cresol;
2,6-di-tert-butyl-4(N,N'-dimethylaminomethylphenol);
4,4'-thiobis (2-methyl-6-tert-butylphenol);
4,4'-thiobis (3 -methyl-6-tert-butylphenol);
2,2'-thiobis (4-methyl-6-tert-butylphenol);
bis(3-methyl-4-hydroxy-5-tert-butylbenzyl) sulfide; and
bis(3,5-di-tert-butyl-4-hydroxybenzyl)sulfide.

Other preferred phenols include hydroquinone; t-butyl hydroquinone; and other derivatives of hydroquinone. The most preferred phenols are hydroquinone and 2,6-di-tert-4-methoxyphenol. Most phenols are commercially available. Mixtures of the phenols may be used in addition to the use of a single phenol.

The term "phenol" as used herein also includes sterically hindered phenols.

For the stabilized dichlorotrifluoroethane, any aromatic or fluorinated alkyl epoxide can be used. Examples of useful aromatic epoxides are of the formula

wherein $R_1$ is hydrogen, alkyl, fluoroalkyl, aryl, fluoroalkyl, or $R_2$; $R_2$ is

and M is phenyl or naphthyl. Preferred aromatic epoxides include butylphenylglycidyl ether; pentylphenylglycidyl ether; hexylphenylglycidyl ether; heptylphenylglycidyl ether; octylphenylglycidyl ether; nonylphenylglycidyl ether; decylphenylglycidyl ether; glycidyl methyl phenyl ether; 1,4-diglycidyl phenyl diether and derivatives thereof; 1,4-diglycidyl naphthyl diether and derivatives thereof; and 2,2'[[[5-heptadecafluorooctyl]1,3phenylene]bis[[2,2,2trifluorome thyl]ethylidene]oxymethylene]bisoxirane. Other preferred aromatic epoxides include naphthyl glycidyl ether, 4-methoxyphenyl glycidyl ether, and derivatives of naphthyl glycidyl ether. The most preferred aromatic epoxide is naphthyl glycidyl ether. Mixtures of aromatic epoxides may be used in addition to the use of a single aromatic epoxide. Most aromatic epoxides are commercially available.

Examples of useful fluorinated alkyl epoxides are of the formula

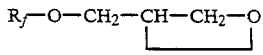

wherein $R_f$ is a fluorinated or perfluorinated alkyl group.

In this system of dichlorotrifluoroethane with phenol and aromatic epoxide, the term "stabilizing amounts" means that total amount of phenol and aromatic or fluorinated alkyl epoxide which stabilizes dichlorotrifluoroethane. Preferably, the total amount of phenol and aromatic or fluorinated alkyl epoxide used is about 0.1 to about 5 percent by weight based on the amount of dichlorotrifluoroethane. The ratio of phenol to aromatic or fluorinated alkyl epoxide can be varied from 1:99 to 99:1.

The stabilized dichlorotrifluoroethane of the present invention may be prepared in any known manner including weighing each component and then mixing the components together.

The stabilized dichlorotrifluoroethane can be used in many applications including as a solvent and a refrigerant.

In another embodiment of the present invention, a stabilized hydrogen-contributing lubricant is formed. Any currently used hydrogen-contributing lubricant can be used. Examples include mineral oil, alkyl benzenes, and polyol esters. Mineral oil, which is paraffin oil or naphthenic oil, is commercially available. Commercially available mineral oils include Witco LP 250 (registered trademark) from Witco, Zerol 300 (registered trademark) from Shrieve Chemical, Sunisco 3GS from Witco, and Calumet R015 from Calumet. Commercially available alkyl benzene lubricants include Zerol 150 (registered trademark). Commercially available esters include neopentyl glycol dipelargonate which is available as Emery 2917 (registered trademark) and Hatcol 2370 (registered trademark). Other useful esters include phosphate esters, dibasic acid esters, and fluoroesters.

For the stabilized hydrogen-contributing lubricant, any phenol and aromatic or fluorinated alkyl epoxide can be used. Preferably, the phenols and aromatic epoxides listed above are used for this embodiment. In this system of hydrogen-contributing lubricant with phenol and aromatic or fluorinated alkyl epoxide, the term "stabilizing amounts" means that total amount of phenol and aromatic or fluorinated alkyl epoxide which stabilizes the hydrogen-contributing lubricant. Preferably, the amount of phenol and aromatic or fluorinated alkyl epoxide used is about 0.01 to about 5 percent by weight based on the amount of the hydrogen-contributing lubricant. The ratio of phenol to aromatic or fluorinated alkyl epoxide can be varied from 1:99 to 99:1.

The stabilized hydrogen-contributing lubricant of the present invention may be prepared in any known manner including weighing each component and then mixing the components together.

In another embodiment of the present invention, a stabilized refrigeration composition is formed. When a hydrogen-contributing lubricant is present in an amount of at least about 0.5 percent by weight based on the R123, the reaction of the R123 and the hydrogen-contributing lubricant occurs. Any currently used hydrogen-contributing lubricants can be used in this embodiment. Preferably, the hydrogen-contributing lubricants which are listed above are used.

Any combination of phenol and aromatic or fluorinated alkyl epoxide which substantially reduces the decomposition of R123 can be used in the stabilized refrigeration composition of the present invention. Preferably, the phenols and aromatic epoxides listed above are used in this embodiment.

Preferably, the amount of phenol and aromatic or fluorinated alkyl epoxide used is about 0.01 to about 5 percent by weight based on the amount of the hydrogen-contributing lubricant. The ratio of phenol to or fluorinated alkyl aromatic epoxide can be varied from 1:99 to 99:1.

The present invention also provides a method for substantially reducing the decomposition of 1,1-dichloro-2,2,2-trifluoroethane in compression refrigeration and air-conditioning equipment using 1,1-dichloro-2,2,2-trifluoroethane as a refrigerant and mineral oil as a lubricant. The method comprises the step of: employing a composition comprising: (i) at least one phenol and (ii) at least one aromatic or fluorinated alkyl epoxide wherein the composition substantially reduces the decomposition of 1,1-dichloro-2,2,2-trifluoroethane.

The present invention is more fully illustrated by the following non-limiting Examples.

EXAMPLES 1 THROUGH 230

The following stabilized R123 compositions are made. In Table I, the abbreviations are as follows:
A-4,4'-methylenebis(2,6-di-tert-butylphenol);
B-4,4'-bis(2,6-di-tert-butylphenol);
C-4,4'-bis(2-methyl-6-tert-butylphenol);
D-2,2'-methylenebis(4-ethyl-6-tert-butylphenol);
E-2,2'-methylenebis(4-methyl-6-tert-butylphenol);
F-4,4'-butylidenebis(3-methyl-6-tert-butylphenol);
G-4,4'-isopropylidenebis(2,6-di-tert-butylphenol);
H-2,2'-methylenebis(4-methyl-6-nonylphenol);
I-2,2'-isobutylidenebis(4,6-dimethylphenol);
J-2,2'-methylenebis(4-methyl-6-cyclohexylphenol);
K-2,6-di-tert-butyl-4-methylphenol;
L-2,6-di-tert-butyl-4-ethylphenol;
M-2,4-dimethyl-6-tert-butylphenol;
N-2,6-di-tert-butyl-α-dimethylamino-p-cresol;
O-2,6-di-tert-butyl-4(N,N'dimethylaminomethylphenol);
P-4,4'-thiobis(2-methyl-6-tert-butylphenol);

Q-4,4'-thiobis(3-methyl-6-tert-butylphenol);
R-2,2'-thiobis(4-methyl-6-tert-butylphenol);
S-bis(3-methyl-4-hydroxy-5-tert-butylbenzyl)sulfide;
T-bis(3,5-di-tert-butyl-4-hydroxybenzyl)sulfide;
U-butylated hydroxytoluene;
V-hydroquinone;
W-t-butyl hydroquinone.
AA-butylphenylglycidyl ether;
BB-pentylphenylglycidyl ether;
CC-hexylphenylglycidyl ether;
DD-heptylphenylglycidyl ether;
EE-octylphenylglycidyl ether;
FF-nonylphenylglycidyl ether;
GG-decylphenylglycidyl ether;
HH-2,2'[[[5-heptadecafluorooctyl]1,3phenylene]-bis-[[2,2,2trifluoromethyl]ethylidene]oxymethylene]-bisoxirane;
II-naphthyl glycidyl ether;
JJ-4-methoxyphenyl glycidyl ether.

TABLE I

| Example | R123 | Phenol | Aromatic Epoxide |
|---|---|---|---|
| 1 | X | A | AA |
| 2 | X | A | BB |
| 3 | X | A | CC |
| 4 | X | A | DD |
| 5 | X | A | EE |
| 6 | X | A | FF |
| 7 | X | A | GG |
| 8 | X | A | HH |
| 9 | X | A | II |
| 10 | X | A | JJ |
| 11 | X | B | AA |
| 12 | X | B | BB |
| 13 | X | B | CC |
| 14 | X | B | DD |
| 15 | X | B | EE |
| 16 | X | B | FF |
| 17 | X | B | GG |
| 18 | X | B | HH |
| 19 | X | B | II |
| 20 | X | B | JJ |
| 21 | X | C | AA |
| 22 | X | C | BB |
| 23 | X | C | CC |
| 24 | X | C | DD |
| 25 | X | C | EE |
| 26 | X | C | FF |
| 27 | X | C | GG |
| 28 | X | C | HH |
| 29 | X | C | II |
| 30 | X | C | JJ |
| 31 | X | D | AA |
| 32 | X | D | BB |
| 33 | X | D | CC |
| 34 | X | D | DD |
| 35 | X | D | EE |
| 36 | X | D | FF |
| 37 | X | D | GG |
| 38 | X | D | HH |
| 39 | X | D | II |
| 40 | X | D | JJ |
| 41 | X | E | AA |
| 42 | X | E | BB |
| 43 | X | E | CC |
| 44 | X | E | DD |
| 45 | X | E | EE |
| 46 | X | E | FF |
| 47 | X | E | GG |
| 48 | X | E | HH |
| 49 | X | E | II |
| 50 | X | E | JJ |
| 51 | X | F | AA |
| 52 | X | F | BB |
| 53 | X | F | CC |
| 54 | X | F | DD |
| 55 | X | F | EE |
| 56 | X | F | FF |
| 57 | X | F | GG |
| 58 | X | F | HH |
| 59 | X | F | II |
| 60 | X | F | JJ |
| 61 | X | G | AA |
| 62 | X | G | BB |
| 63 | X | G | CC |
| 64 | X | G | DD |
| 65 | X | G | EE |
| 66 | X | G | FF |
| 67 | X | G | GG |
| 68 | X | G | HH |
| 69 | X | G | II |
| 70 | X | G | JJ |
| 71 | X | H | AA |
| 72 | X | H | BB |
| 73 | X | H | CC |
| 74 | X | H | DD |
| 75 | X | H | EE |
| 76 | X | H | FF |
| 77 | X | H | GG |
| 78 | X | H | HH |
| 79 | X | H | II |
| 80 | X | H | JJ |
| 81 | X | I | AA |
| 82 | X | I | BB |
| 83 | X | I | CC |
| 84 | X | I | DD |
| 85 | X | I | EE |
| 86 | X | I | FF |
| 87 | X | I | GG |
| 88 | X | I | HH |
| 89 | X | I | II |
| 90 | X | I | JJ |
| 91 | X | J | AA |
| 92 | X | J | BB |
| 93 | X | J | CC |
| 94 | X | J | DD |
| 95 | X | J | EE |
| 96 | X | J | FF |
| 97 | X | J | GG |
| 98 | X | J | HH |
| 99 | X | J | II |
| 100 | X | J | JJ |
| 101 | X | K | AA |
| 102 | X | K | BB |
| 103 | X | K | CC |
| 104 | X | K | DD |
| 105 | X | K | EE |
| 106 | X | K | FF |
| 107 | X | K | GG |
| 108 | X | K | HH |
| 109 | X | K | II |
| 110 | X | K | JJ |
| 111 | X | L | AA |
| 112 | X | L | BB |
| 113 | X | L | CC |
| 114 | X | L | DD |
| 115 | X | L | EE |
| 116 | X | L | FF |
| 117 | X | L | GG |
| 118 | X | L | HH |
| 119 | X | L | II |
| 120 | X | L | JJ |
| 121 | X | M | AA |
| 122 | X | M | BB |
| 123 | X | M | CC |
| 124 | X | M | DD |
| 125 | X | M | EE |
| 126 | X | M | FF |
| 127 | X | M | GG |
| 128 | X | M | HH |
| 129 | X | M | II |
| 130 | X | M | JJ |
| 131 | X | N | AA |
| 132 | X | N | BB |
| 133 | X | N | CC |
| 134 | X | N | DD |
| 135 | X | N | EE |
| 136 | X | N | FF |
| 137 | X | N | GG |
| 138 | X | N | HH |

TABLE I-continued

| Example | R123 | Phenol | Aromatic Epoxide |
|---|---|---|---|
| 139 | X | N | II |
| 140 | X | N | JJ |
| 141 | X | O | AA |
| 142 | X | O | BB |
| 143 | X | O | CC |
| 144 | X | O | DD |
| 145 | X | O | EE |
| 146 | X | O | FF |
| 147 | X | O | GG |
| 148 | X | O | HH |
| 149 | X | O | II |
| 150 | X | O | JJ |
| 151 | X | P | AA |
| 152 | X | P | BB |
| 153 | X | P | CC |
| 154 | X | P | DD |
| 155 | X | P | EE |
| 156 | X | P | FF |
| 157 | X | P | GG |
| 158 | X | P | HH |
| 159 | X | P | II |
| 160 | X | P | JJ |
| 161 | X | Q | AA |
| 162 | X | Q | BB |
| 163 | X | Q | CC |
| 164 | X | Q | DD |
| 165 | X | Q | EE |
| 166 | X | Q | FF |
| 167 | X | Q | GG |
| 168 | X | Q | HH |
| 169 | X | Q | II |
| 170 | X | Q | JJ |
| 171 | X | R | AA |
| 172 | X | R | BB |
| 173 | X | R | CC |
| 174 | X | R | DD |
| 175 | X | R | EE |
| 176 | X | R | FF |
| 177 | X | R | GG |
| 178 | X | R | HH |
| 179 | X | R | II |
| 180 | X | R | JJ |
| 181 | X | S | AA |
| 182 | X | S | BB |
| 183 | X | S | CC |
| 184 | X | S | DD |
| 185 | X | S | EE |
| 186 | X | S | FF |
| 187 | X | S | GG |
| 188 | X | S | HH |
| 189 | X | S | II |
| 190 | X | S | JJ |
| 191 | X | T | AA |
| 192 | X | T | BB |
| 193 | X | T | CC |
| 194 | X | T | DD |
| 195 | X | T | EE |
| 196 | X | T | FF |
| 197 | X | T | GG |
| 198 | X | T | HH |
| 199 | X | T | II |
| 200 | X | T | JJ |
| 201 | X | U | AA |
| 202 | X | U | BB |
| 203 | X | U | CC |
| 204 | X | U | DD |
| 205 | X | U | EE |
| 206 | X | U | FF |
| 207 | X | U | GG |
| 208 | X | U | HH |
| 209 | X | U | II |
| 210 | X | U | JJ |
| 211 | X | V | AA |
| 212 | X | V | BB |
| 213 | X | V | CC |
| 214 | X | V | DD |
| 215 | X | V | EE |
| 216 | X | V | FF |
| 217 | X | V | GG |
| 218 | X | V | HH |
| 219 | X | V | II |
| 220 | X | V | JJ |
| 221 | X | W | AA |
| 222 | X | W | BB |
| 223 | X | W | CC |
| 224 | X | W | DD |
| 225 | X | W | EE |
| 226 | X | W | FF |
| 227 | X | W | GG |
| 228 | X | W | HH |
| 229 | X | W | II |
| 230 | X | W | JJ |

EXAMPLES 231–460

Stabilized mineral oil is prepared by replacing the R123 of each Example 1 through 230 with mineral oil.

EXAMPLES 461–690

Mineral oil is added to each composition of Examples 1 through 230 to form a stabilized refrigeration composition.

COMPARATIVES A THROUGH I AND EXAMPLES 691–693

The stability of a refrigeration system that uses R123 with hydrogen-contributing lubricants can be measured using three criteria which are visual appearance, the amount of HCFC-133a formed, and the amount of chloride and fluoride ions formed. In the following Comparatives and Examples, all three criteria were used to judge the stability of the systems.

The stability tests were conducted using a sealed tube procedure. The refrigerant and lubricant were sealed in a glass tube with aluminum and copper. The tubes were put into an oven at 149° C. for 2 weeks. The tubes were removed from the oven, visually inspected, and then opened. The refrigerant was collected and analyzed by gas chromatography. The oil and metal parts in the tubes were washed with hexane and a buffer solution. The hexane solution was then extracted with the same buffer solution. The buffer solutions were joined and analyzed for chloride and fluoride ions using gel permeation chromatography.

The results are in Table II below. C-A stands for Comparative A, C-B stands for Comparative B, C-C stands for Comparative C, C-D stands for Comparative D, C-E stands for Comparative E, C-F stands for Comparative F, C-G stands for Comparative G, C-H stands for Comparative H, and C-I stands for Comparative I. Stab stands for Stabilizer. Visual stands for visual appearance.

The lubricant used was mineral oil. The ratio of R123 to lubricant was 1:1.

In Table II, the abbreviations of the stabilizers are as follows:
I-butylated hydroxytoluene;
II-hydroxyquinone;
III-glycidyl isopropylether;
IV-glydicyl methylphenyl ether;
V-glycidyl naphthyl ether; and
VI-2,2'[[[5-heptadecafluorooctyl]1,3phenylene]bis-[[2,2,2trifluoromethyl]ethylidene]oxymethylene]-bisoxirane.

Also in Table II, "Decomp" means the (percent decomposition of R123 with additives)/(percent decomposition of R123 without additives). "Acid" means the (concentration of hydrogen chloride and hydrogen fluoride acid formed with additives)/(concentration of hydrogen chloride and hydrogen fluoride acid formed without additives). The percent decomposition of R123 reflects the amount of HCFC-133a formed.

In Table II, D means discolored, HD means highly discolored, and U means unchanged.

TABLE II

|     | Stab      | Visual | Decomp | Acid |
|-----|-----------|--------|--------|------|
| C-A | none      | D      | 1      | 1    |
| C-B | I         | D      | 0.48   | 0.79 |
| C-C | II        | D      | 0.33   | 0.65 |
| C-D | IV        | D      | 1.77   | 0.63 |
| C-E | V         | HD     | 1.04   | 0.51 |
| C-F | VI        | HD     | 0.79   | 1.35 |
| C-G | I + III   | HD     | 1.02   | 1.44 |
| C-H | II + III  | HD     | 4.17   | 3.26 |
| C-I | II + V    | HD     | 1.96   | 1.84 |
| E-1 | I + IV    | U      | 0.24   | 0.12 |
| E-2 | I + V     | U      | 0.16   | 0.03 |
| E-3 | II + VI   | U      | 0.19   | 0.15 |

Comparative A was a baseline experiment for the stability of R123 with mineral oil. The art is looking for any reduction in the formation of HCFC-133a. The ratios in the other Comparatives and Examples are given as a fraction of the baseline experiment. Thus, in Comparative B for example, the decomposition ratio was 0.46 times that of the corresponding baseline experiment.

In Comparatives B and C, a phenol alone was added to the R123 and lubricant. The results demonstrate that a phenol alone does not substantially reduce the decomposition of R123.

In Comparatives D through F, an epoxide alone was added to the R123 and lubricant. The results demonstrate that an epoxide alone does not substantially reduce the decomposition of R123.

In Comparatives G and H, a phenol and non-aromatic epoxide were added to the R123 and lubricant. The results demonstrate that a phenol and non-aromatic epoxide do not substantially reduce the decomposition of R123. We believe that these results were due to the use of a non-aromatic epoxide.

In Example 1, a phenol and aromatic epoxide were added to the composition of R123 and mineral oil. When used alone in Comparatives B and D, the phenol and aromatic epoxide were shown to be ineffective in substantially reducing the decomposition of R123. The combination though is very effective in reducing the decomposition of R123.

In Example 2, another aromatic epoxide and phenol were added to the composition of R123 and mineral oil. When used alone in Comparatives B and E, the phenol and aromatic epoxide were shown to be ineffective in substantially reducing the decomposition of R123. The combination though is very effective in reducing the decomposition of R123.

In Example 3, another phenol and another aromatic epoxide were added to the composition of R123 and mineral oil. When used alone in Comparatives C and F, the phenol and aromatic epoxide were shown to be ineffective in substantially reducing the decomposition of R123. The combination though is very effective in substantially reducing the decomposition of R123.

Having described the invention in detail and by reference to preferred embodiments thereof, it will be apparent that modifications and variations are possible without departing from the scope of the invention defined in the appended claims.

What is claimed is:

1. A compositions comprising:
   (a) 1,1-dichloro-2,2,2-trifluoroethane; and
   (b) at least one hydrogen-contributing lubricant selected from the group consisting of mineral oil, alkyl benzene, and ester; and
   (c) a composition comprising (i) at least one phenol or derivative thereof and (ii) at least one aromatic or fluorinated alkyl epoxide wherein said composition (c) substantially reduces the decomposition of said 1,1-dichloro-2,2,2-trifluoroethane.

2. The composition of claim 1 wherein said hydrogen-contributing lubricant is mineral oil.

3. The composition of claim 1 wherein said phenol or a derivative thereof selected from the group consisting of:
   4,4'-methylenebis(2,6-di-tert-butylphenol);
   4,4'-bis( 2,6-di-tert-butylphenol);
   4,4'-bis(2-methyl-6-tert-butylphenol);
   2,2'-methylenebis(4-ethyl-6-tert-butylphenol);
   2,2'-methylenebis (4-methyl-6-tert-butylphenol);
   4,4'-butylidenebis(3-methyl-6-tert-butylphenol);
   4,4'-isopropylidenebis(2,6-di-tert-butylphenol);
   2,2'-methylenebis(4-methyl-6-nonylphenol);
   2,2'-isobutylidenebis( 4, 6-dimethylphenol);
   2,2'-methylenebis (4-methyl-6-cyclohexylphenol);
   2,6-di-tert-butyl-4-methylphenol;
   2,6-di-tert-butyl-4-ethylphenol;
   2,4-dimethyl-6-tert-butylphenol;
   2,6-di-tert-butyl-α-dimethylamino-p-cresol;
   2,6-di-tert-butyl-4( N,N'-dimethylaminomethylphenol);
   4,4'-thiobis (2-methyl-6-tert-butylphenol);
   4,4'-thiobis(3-methyl-6-tert-butylphenol);
   2,2'-thiobis(4-methyl-6-tert-butylphenol);
   bis(3-methyl-4-hydroxy-5-tert-butylbenzyl)sulfide;
   bis(3,5-di-tert-butyl-4-hydroxybenzyl)sulfide; hydroquinone; t-butyl hydroquinone; derivatives of hydroquinone; and mixtures thereof.

4. The composition of claim 1 wherein said phenol or a derivative thereof selected from the group consisting of hydroquinone and 2,6-di-tert-butyl-4-methylphenol.

5. The composition of claim 1 wherein said aromatic epoxide is selected from the group consisting of butylphenylglycidyl ether; pentylphenylglycidyl ether; hexylphenylglycidyl ether; heptylphenylglycidyl ether; octylphenylglycidyl ether; nonylphenylglycidyl ether; decylphenylglycidyl ether; 2,2'[[[5-heptadecafluorooctyl]1,3phenylene]bis-[[2,2,2trifluoromethyl]ethylidene]-oxymethylene]bisoxirane; naphthyl glycidyl ether; 4-methoxyphenyl glycidyl ether; derivatives of naphthyl glycidyl ether; glycidyl methyl phenyl ether; 1,4-diglycidyl phenyl ether and derivatives thereof; 1,4-diglycidyl naphthyl ether and derivatives thereof; and mixtures thereof.

6. The composition of claim 1 wherein said aromatic epoxide is naphthyl glycidyl ether.

7. The composition of claim 1 wherein the amount of said phenol and aromatic epoxide is about 0.01 to about 5 percent by weight based on the amount of said hydrogen-contributing lubricant.

8. A composition comprising:
   (a) 1,1-dichloro-2,2,2-trifluoroethane; and
   (b) at least one hydrogen-contributing lubricant selected from the group consisting of mineral oil, alkyl benzene, and ester; and
   (c) a composition consisting essentially of (i) at least one phenol or derivative thereof and (ii) at least one aromatic or fluorinated alkyl epoxide wherein said composition (c) substantially reduces the decomposition of said 1,1-dichloro-2,2,2-trifluoroethane.

* * * * *